US008039442B2

(12) United States Patent
Magnani

(10) Patent No.: US 8,039,442 B2
(45) Date of Patent: Oct. 18, 2011

(54) COMPOUNDS AND METHODS FOR TREATMENT OF SICKLE CELL DISEASE OR COMPLICATIONS ASSOCIATED THEREWITH

(75) Inventor: John L Magnani, Gaithersburg, MD (US)

(73) Assignee: GlycoMimetics, Inc., Gaithersburg, MD (US)

( * ) Notice: Subject to any disclaimer, the term of this patent is extended or adjusted under 35 U.S.C. 154(b) by 441 days.

(21) Appl. No.: 12/218,213

(22) Filed: Jul. 11, 2008

(65) Prior Publication Data

US 2009/0023679 A1 Jan. 22, 2009

Related U.S. Application Data

(60) Provisional application No. 60/959,984, filed on Jul. 18, 2007.

(51) Int. Cl.
*A61K 31/7034* (2006.01)

(52) U.S. Cl. ........................................................ 514/35

(58) Field of Classification Search ........................ None
See application file for complete search history.

(56) References Cited

U.S. PATENT DOCUMENTS 4,471,057 A 9/1984 Koprowski et al. ........... 436/518
4,851,511 A 7/1989 Hakomori et al. ............ 530/387
4,859,769 A 8/1989 Karlsson et al. ................ 536/53
4,876,199 A 10/1989 Hakamori ..................... 530/387
4,925,796 A 5/1990 Bergh et al. ...................... 435/97
4,946,830 A 8/1990 Pulverer et al. ................. 514/23
5,143,712 A 9/1992 Brandley et al. ............... 424/1.1
5,151,360 A 9/1992 Handa et al. ............... 435/240.2
5,211,937 A 5/1993 Brandley et al. ............... 424/1.1
5,268,364 A 12/1993 Kojima et al. .................. 514/25
5,304,640 A 4/1994 Lasky et al. .................. 536/23.5
5,352,670 A 10/1994 Venot et al. ..................... 514/54
5,369,096 A 11/1994 Yamada et al. ................. 514/61
5,412,123 A 5/1995 Rao et al. ...................... 552/290
5,444,050 A 8/1995 Kogan et al. .................... 514/25
5,464,778 A 11/1995 Cummings et al. ........... 436/503
5,464,815 A 11/1995 Chamow et al. .................. 514/8
5,470,843 A 11/1995 Stahl et al. ...................... 514/61
5,484,891 A 1/1996 Lasky et al. ................ 530/387.3
5,486,536 A 1/1996 Ward et al. ..................... 514/460
5,519,008 A 5/1996 Rao et al. ........................ 514/26
5,527,785 A 6/1996 Bevilacqua et al. ............ 514/56
5,538,724 A 7/1996 Butcher et al. ............. 424/152.1
5,559,103 A 9/1996 Gaeta et al. ..................... 514/54
5,576,305 A 11/1996 Ratcliffe .......................... 514/25
5,580,858 A 12/1996 Ippolito et al. .................. 514/25
5,580,862 A 12/1996 Rosen et al. .................... 514/61
5,589,465 A 12/1996 Ishida et al. .................... 514/25
5,604,207 A 2/1997 DeFrees et al. ................. 514/25
5,618,785 A 4/1997 Heavner et al. .................. 514/2
5,622,937 A 4/1997 Kogan et al. .................... 514/25
5,639,734 A 6/1997 Esko et al. ...................... 514/25
5,646,123 A 7/1997 Ippolito et al. .................. 514/25
5,646,248 A 7/1997 Sawada et al. ................ 530/350
5,648,344 A 7/1997 Brandley et al. ................ 514/61
5,654,282 A 8/1997 Tang et al. ....................... 514/25
5,654,412 A 8/1997 Srivastava et al. ........... 536/18.5
5,658,880 A 8/1997 Dasgupta et al. ................. 514/8
5,663,151 A 9/1997 Martel et al. .................... 514/25
5,679,321 A 10/1997 Dasgupta et al. .............. 424/9.1
5,679,644 A 10/1997 Rao et al. ........................ 514/26
5,686,426 A 11/1997 Martel et al. .................... 514/25
5,693,621 A 12/1997 Toepfer et al. .................. 514/25
5,695,752 A 12/1997 Rosen et al. ............... 424/94.61
5,710,023 A 1/1998 Collins et al. ................ 435/69.1
5,710,123 A 1/1998 Heavner et al. .................. 514/2
5,723,583 A 3/1998 Seed et al. ................. 530/387.3
5,728,685 A 3/1998 Abbas et al. .................... 514/53
5,739,300 A 4/1998 Toepfer et al. ................. 536/4.1
5,747,463 A 5/1998 Marinier et al. ................ 514/25
5,750,508 A 5/1998 Dasgupta et al. ............... 514/25
5,753,617 A 5/1998 Heavner et al. .................. 514/9
5,753,631 A 5/1998 Paulson et al. .................. 514/25
5,763,413 A 6/1998 Numata et al. .................. 514/25
5,763,582 A 6/1998 Rao et al. .......................... 536/5
5,789,385 A 8/1998 Anderson et al. ............... 514/25
5,789,573 A 8/1998 Baker et al. .................. 536/24.5
5,795,958 A 8/1998 Rao et al. ...................... 530/331
5,811,404 A 9/1998 De Frees et al. ................ 514/25
5,811,405 A 9/1998 Toepfer et al. .................. 514/25
5,817,742 A 10/1998 Toepfer et al. ................ 528/328
5,827,817 A 10/1998 Larsen et al. ..................... 514/2
5,827,837 A 10/1998 Bevilacqua et al. .......... 514/103
5,830,871 A 11/1998 Wong et al. ..................... 514/23
5,837,689 A 11/1998 Anderson et al. ............... 514/25

(Continued)

FOREIGN PATENT DOCUMENTS

EP 319253 A2 6/1989

(Continued)

OTHER PUBLICATIONS

Chang, J. et al "GMI-1070, a novel pan-selectin antagonist . . . " Blood (2010) vol. 116, No. 10, pp. 1779-1786.* Ferrara, J. et al "Graft-versus-host disease" The Lancet (2009) vol. 373, pp. 1550-1561.*

Li, B. et al "Delaying acute graft-versus-host disease . . . " Scand. J. Immunol. (2004) vol. 59, pp. 464-468.*

Patton, J.T. et al., "GMI-1070: a Small Glycomimetic, Pan-selectin Antagonist that Improves Blood Flow and Inhibits Blood Cell Adhesion in Sickle Mice," *Abstract ID:ABSTY-5APYL-CA6TP-V2ET6*, Sep. 2, 2005.

Abraham, W.M. et al., "Selectin Blockade Prevents Antigen-induced Late Bronchial Response and Airway Hyperresponsiveness in Allergic Sheep," *Am J. Respir Crit Care Med.* 159: 1205-1214, 1999.

Acord, J. et al., "A rapid microplate method for quantifying inhibition of bacterial adhesion to eukaryotic cells," *Journal of Microbiological Methods* 60: 55-62, 2005.

Baeckström et al., "Purification and Characterization of a Membrane-bound and a Secreted Mucin-type Glycoprotein Carrying the Carcinoma-associated Sialyl-Le$^a$ Epitope on Distinct Core Proteins," *J. Biol. Chem.* 266(32):21537-21547, 1991.

(Continued)

*Primary Examiner* — Leigh Maier
(74) *Attorney, Agent, or Firm* — Seed IP Law Group PLLC

(57) ABSTRACT

Compounds, compositions and methods are provided for treatment of sickle cell disease or a complication associated therewith, or graft versus host disease, in an individual. More specifically, the use of particular glycomimetics for the treatment is described.

5 Claims, 10 Drawing Sheets

U.S. PATENT DOCUMENTS 5,837,690 A 11/1998 Rao et al. ........ 514/26
5,840,679 A 11/1998 Larsen et al. ........ 514/8
5,854,218 A 12/1998 DeFrees ........ 514/25
5,858,983 A 1/1999 Seed et al. ........ 514/23
5,858,994 A 1/1999 Kretzschmar et al. ........ 514/62
5,880,091 A 3/1999 Cummings et al. ........ 514/8
5,916,910 A 6/1999 Lai ........ 514/423
5,919,768 A 7/1999 Korgan et al. ........ 514/25
5,919,769 A 7/1999 Tsukida et al. ........ 514/25
5,962,422 A 10/1999 Nagy et al. ........ 514/25
5,976,540 A 11/1999 Rittershaus et al. ........ 424/184.1
5,977,080 A 11/1999 Rosen et al. ........ 514/25
5,985,852 A 11/1999 Nagy et al. ........ 514/54
5,994,402 A 11/1999 Rotstein et al. ........ 514/547
6,001,819 A 12/1999 Simon et al. ........ 514/54
6,001,988 A 12/1999 Parma et al. ........ 536/24.3
6,033,665 A 3/2000 Yednock et al. ........ 424/130.1
6,037,333 A 3/2000 Panjwani ........ 514/62
6,110,897 A 8/2000 Unverzagt et al. ........ 514/25
6,111,065 A 8/2000 Heavner et al. ........ 530/300
6,120,751 A 9/2000 Unger ........ 424/9.51
6,121,233 A 9/2000 Magnani et al. ........ 514/8
6,124,267 A 9/2000 Mc Ever et al. ........ 514/25
6,133,239 A 10/2000 Handa et al. ........ 514/25
6,133,240 A 10/2000 Taylor et al. ........ 514/25
6,136,790 A 10/2000 Toepfer et al. ........ 514/25
6,169,077 B1 1/2001 Oehrlein ........ 514/25
6,177,547 B1 1/2001 Cummings et al. ........ 530/388.22
6,187,754 B1 2/2001 Oehrlein ........ 514/25
6,193,973 B1 2/2001 Tuttle ........ 424/195.1
6,193,979 B1 2/2001 Rittershaus et al. ........ 424/195.11
6,197,752 B1 3/2001 Schmidt et al. ........ 514/23
6,225,071 B1 5/2001 Cummings et al. ........ 435/7.24
6,235,309 B1 5/2001 Nagy et al. ........ 424/450
6,280,932 B1 8/2001 Parma et al. ........ 435/6
6,309,639 B1 10/2001 Cummings et al. ........ 424/143.1
6,387,884 B1 5/2002 Magnani et al. ........ 514/25
6,391,857 B1 5/2002 Magnani et al. ........ 514/25
6,407,135 B1 6/2002 Lai et al. ........ 514/423
6,465,434 B1 10/2002 Magnani et al. ........ 514/23
6,492,332 B1 12/2002 Demopulos et al. ........ 514/12
6,503,885 B1 1/2003 Kiso et al. ........ 514/25
6,528,487 B1 3/2003 Heavner et al. ........ 514/13
2001/0046970 A1 11/2001 Nagy et al. ........ 514/53
2001/0051370 A1 12/2001 Bistrup et al. ........ 435/193
2002/0026033 A1 2/2002 Cummings et al. ........ 530/322
2002/0028205 A1 3/2002 Holgersson et al. ........ 424/184.1
2002/0031508 A1 3/2002 Wagner et al. ........ 424/94.63
2002/0040008 A1 4/2002 Wagner et al. ........ 514/41
2002/0132220 A1 9/2002 Berens et al. ........ 435/1.1
2002/0164336 A1 11/2002 Harrison et al. ........ 424/146.1
2002/0164748 A1 11/2002 Bistrup et al. ........ 435/193
2002/0168366 A1 11/2002 Stewart et al. ........ 424/146.1
2003/0012787 A1 1/2003 Ashkenazi et al. ........ 424/145.1
2003/0012790 A1 1/2003 Ashkenazi et al. ........ 424/178.1
2003/0018181 A1 1/2003 Larsen et al. ........ 536/23.4
2003/0039683 A1 2/2003 Cantrell et al. ........ 424/450
2005/0112124 A1 5/2005 Frenette et al. ........ 424/144.1
2005/0187171 A1 8/2005 Magnani et al. ........ 514/43
2007/0054870 A1 3/2007 Magnani et al. ........ 514/35
2008/0112955 A1 5/2008 Embury et al. ........ 424/133.1
2008/0200406 A1 8/2008 Magnani ........ 514/35

FOREIGN PATENT DOCUMENTS

EP 381310 A1 8/1990
EP 408859 B1 8/1995
EP 671407 A2 9/1995
WO WO 90/13300 11/1990
WO WO 91/19502 12/1991
WO WO 92/01718 2/1992
WO WO 92/07572 5/1992
WO WO 94/26760 11/1994
WO WO 94/29477 12/1994
WO WO 95/03059 2/1995
WO WO 95/29681 11/1995
WO WO 96/20204 7/1996
WO WO 96/25418 8/1996
WO WO 96/26950 9/1996
WO WO 97/01335 1/1997
WO WO 97/01569 1/1997
WO WO 97/14707 4/1997
WO WO 97/28173 8/1997
WO WO 97/28174 8/1997
WO WO 98/06730 2/1998
WO WO 98/13058 4/1998
WO WO 99/42130 8/1999
WO WO 99/43353 9/1999
WO WO 99/43356 9/1999
WO WO 01/89564 11/2001
WO WO 02/22820 3/2002
WO WO 02/062810 8/2002
WO WO 03/088980 A1 10/2003
WO WO 03/097658 11/2003
WO WO 2004/004636 1/2004
WO WO 2004/058304 7/2004
WO WO 2005/054264 6/2005
WO WO 2006/127906 11/2006
WO WO 2007/028050 3/2007

OTHER PUBLICATIONS

Bänteli, R. et al., "Potent E-Selectin Antagonists," *Helvetica Chimica Acta* 83(11): 2893-2907, 2000.

Belcher, J.D. et al., "Activated monocytes in sickle cell disease: potential role in the activation of vascular endothelium and vaso-occlusion," *Blood* 96(7):2451-2459, Oct. 1, 2000.

Belcher, J.D. et al., "Inflammatory response in transgenic mouse models of human sickle cell anemia," *Blood* 96(11)Pt.1:600a, Abstract #2574, Nov. 16, 2000.

Berg et al., "A Carbohydrate Domain Common to Both Sialyl $Le^a$ and Sialyl $Le^x$ Is Recognized by the Endothelial Cell Leukocyte Adhesion Molecule ELAM-1," *J. Biol. Chem.* 266(23):14869-14872, 1991.

Berg et al., "The Cutaneous Lymphocyte Antigen Is a Skin Lymphocyte Homing Receptor for the Vascular Lectin Endothelial Cell-Leukocyte Adhesion Molecule 1,"*J. Exp. Med.* 174:1461-1466, 1991.

Bird and Kimber, "Oligosaccharides Containing Fucose Linked α(1-3) and α(1-4) to *N*-Acetylglucosamine Cause Decompaction of Mouse Morulae," *Devel. Biol.* 104:449-460, 1984.

Bowen et al., "Characterization of a Human Homologue of the Murine Peripheral Lymph Node Homing Receptor," *Journal of Cell Biology* 109:421-427, 1989.

Brandley et al., "Carbohydrate Ligands of LEC Cell Adhesion Molecules," *Cell* 63:861-863, 1990.

Broquet et al., "Effect of Desipramine on a Glycoprotein Sialyltransferase Activity in C6 Cultured Glioma Cells," *J. Neurochem.* 54:388-394, 1990.

Ceder, O. et al., "On the Absolute Configuration of 3-Cyclohexene-1-carboxylic Acid," *Acta Chemica Scandinavica* 24(8):2693-2698, 1970.

Childs et al., "High-molecular-weight glycoproteins are the major carriers of the carbohydrate differentiation antigens I, i and SSEA-1 of mouse teratocarcinoma cells," *Biochem. J.* 215:491-503, 1983.

Cleophax, J. et al., "A Chiral Synthesis of D-(+)-2,6-Dideoxystreptamine and Its Microbial Incorporation into Novel Antibiotics," *Journal of the American Chemical Society* 98(22): 7110-7112, Oct. 27, 1976.

Corral et al., "Requirements for Sialic Acid on Neutrophils in a GMP-140 (PADGEM) Mediated Adhesive Interaction with Activated Platelets," *Biochem. Biophys. Res. Commun.* 172:1349-1356, 1990.

Datta and Takayama, "Isolation and purification of trehalose 6-mono- and 6,6'-di-corynomycolates from *Cornyebacterium matruchotii*. Structural characterization of $^{1}$H NMR," *Carbohydrate Research* 245: 151-158, 1993.

Duijvestijn et al., "High Endothelial Differentiation in Human Lymphoid and Inflammatory Tissues Defined by Monoclonal Antibody HECA-452," *Am. J. Path.* 130:147-155, 1988.

Dupré, B. et al., "Glycomimetic Selectin Inhibitors: (α-D-Mannopyranosyloxy)methylbiphenyls,"*Bioorganic & Medicinal Chemistry Letters* 6(5): 569-572, 1996.

Edgington, "How Sweet It Is: Selectin-Mediating Drugs," *Biotechnology* 10: 383-389, 1992.

Eggens et al., "A Role of Carbohydrate-Carbohydrate Interaction in the Process of Specific Cell Recognition During Embryogenesis and Organogenesis: A Preliminary Note," *Biochem. Biophys. Res. Commun.* 158(3):913-920, 1989.
Eggens et al., "Specific Interaction between $Le^x$ and $Le^x$ Determinants. A Possible Basis for Cell Recognition in Preimplantation Embryos and in Embryonal Carcinoma Cells," *J. Biol. Chem.* 264(16):9476-9484, 1989.
Embury, S.H. et al., "The contribution of endothelial cell P-selectin to the microvascular flow of mouse sickle erythrocytes in vivo," *Blood* 104(10):3378-3385, Nov. 15, 2004.
Ernst and Oehrlein, "Substrate and donor specificity of glycosyl transferases," *Glycoconjugate Journal* 16: 161-170, 1999.
Fenderson et al., "A Multivalent Lacto-*N*-Fucopenataose III-Lysyllysine Conjugate Decompacts Preimplantation Mouse Embryos, While the Free Oligosaccharide is Ineffective," *J. Exp. Med.* 160:1591-1596, 1984.
Fenderson et al., "Coordinate Expression of X and Y Haptens during Murine Embryogenesis,"*Devel. Biol.* 114:12-21, 1986.
Fenderson et al., "The blood group I antigen defined by monoclonal antibody *C6* is a marker of early mesoderm during murine embryogenesis," *Differentiation* 38:124-133, 1988.
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," *J. Biol. Chem.* 259(7):4681-4685, 1984.
Fukushi et al., "Novel Fucolipids Accumulating in Human Adenocarcinoma. III. A Hybridoma Antibody (FH6) Defining a Human Cancer-Associated Difucoganglioside ($VI^3NeuAcV^3III$ $^3Fuc_2nLc_6$)," *J. Biol. Chem.* 259(16):10511-10517, 1984.
Gabius et al., "Endogenous Tumor Lectins: Overview and Perspectives," *Anticancer Res.* 6:573-578, 1986.
Gais, H.-J. et al., "Enantioselective and Enantioconvergent Syntheses of Building Blocks for the Total Synthesis of Cyclopentanoid Natural Products," *Angewandte Chemie, Int. Ed. Eng.* 23(2):142-143, 1984.
Gallatin et al., "A cell-surface molecule involved in organ-specific homing of lymphocytes," *Nature* 304:30-34, 1983.
Gooi et al., "Stage-specific embryonic antigen involves α1 → 3 fucosylated type 2 blood group chains," *Nature* 292:156-158, 1981.
Hakomori et al., "Novel Fucolipids Accumulating in Human Adenocarcinoma. I. Glycolipids With Di- or Trifucosylated Type 2 Chain," *J. Biol. Chem.* 259(7):4672-4680, 1984.
Hakomori et al., "The Hapten Structure of a Developmentally Regulated Glycolipid Antigen (SSEA-1) Isolated From Human Erythrocytes and Adenocarcinoma: A Preliminary Note," *Biochem. Biophys. Res. Comm.* 100(4):1578-1586, 1981.
Hakomori S., "Aberrant Glycosylation in Cancer Cell Membranes as Focused on Glycolipids: Overview and Perspectives," *Cancer Res.* 45:2405-2414, 1985.
Handa et al., "Selectin GMP-140 (CD62; PADGEM) Binds to Sialosyl -$Le^a$ and Sialosyl-$Le^x$, and Sulfated Glycans Modulate this Binding," *Biochemical and Biophysical Research Communication* 181(3):1223-1230, 1991.
Hansson and Zopf, "Biosynthesis of the Cancer-associated Sialyl-$Le^a$ Antigen," *Journal of Biological Chemistry* 260(16):9388-9392, 1985.
Harlan, J.M., "Introduction-anti-adhesion therapy in sickle cell disease," *Blood* 95: 365-367, 2000.
Hasegawa et al., "Synthesis of deoxy-L-fucose-containing sialyl Lewis X ganglioside analogues," *Carbohydrate Research* 257: 67-80, 1994.
Hasegawa et al., "Synthesis of sialyl Lewis X ganglioside analogues containing modified L-fucose residues," *Carbohydrate Research* 274: 165-181, 1995.
Hebbel, R.P., "Blockade of Adhesion of Sickle Cells to Endothelium by Monoclonal Antibodies," *The New England Journal of Medicine* 342:1910-1912, Jun. 22, 2000.
Holmes et al., "Enzymatic Basis for the Accumulation of Glycolipids with X and Dimeric X Determinants in Human Lung Cancer Cells (NCI-H69)," *J. Biol. Chem.* 260(12):7619-7627, 1985.
Huse et al., "Generation of a Large Combinatorial Library of the Immunoglobulin Repertoire in Phage Lambda," *Science* 246:1275-1281, 1989.
Hynes, R., "Integrins: A Family of Cell Surface Receptors," *Cell* 48:549-554, 1987.
Inwald, D.P. et al., "Platelet and leukocyte activation in childhood sickle cell disease: association with nocturnal hypoxaemia," *British Journal of Haematology* 111:474-481, Nov. 2000.
Issekutz, T., "Inhibition of in Vivo Lymphocyte Migration of Inflammation and Homing to Lymphoid Tissues by the TA-2 Monoclonal Antibody. A Likely Role for VLA-4 in Vivo," *Journal of Immunology* 147:4178-4184, 1991.
Itai, S. et al., "Differentiation-dependent Expression of I and Sialyl I Antigens in the Developing Lung of Human Embryos and in Lung Cancers," *Cancer Research* 50: 7603-7611, 1990.
Jeffrey et al., "Affinity Chromatography of Carbohydrate-Specific Immunoglobulins: Coupling of Oligosaccharides to Sepharose ," *Biochem. Biophys. Res. Commun.* 62:608-613, 1975.
Jentsch, K.D. et al., "Inhibition of Human Immunodeficiency Virus Type I Reverse Transcriptase by Suramin-related Compounds," *The Journal of General Virology* 68(8): 2183-2192, 1987.
Kaila, N. et al., "Design and Synthesis of Sialyl $Lewis^x$ Mimics as E- and P-Selectin Inhibitors," *Medicinal Research Reviews* 22(6): 566-601, 2002.
Kannagi et al., "New Globoseries Glycosphingolipids in Human Teratocarcinoma Reactive with the Monoclonal Antibody Directed to a Developmentally Regulated Antigen, Stage-specific Embryonic Antigen 3," *J. Biol. Chem.* 258(14):8934-8942, 1983.
Kannagi et al., "Stage-specific embryonic antigens (SSEA-3 and -4) are epitopes of a unique globo-series ganglioside isolated from human teratocarcinoma cells," *Embo J.* 2(12):2355-2361, 1983.
Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," *Cancer Biochem. Biophys.* 11:311-315, 1990.
Kaul, D.K. et al., "Hypoxia/reoxygenation causes inflammatory response in transgenic sickle mice but not in normal mice," *The Journal of Clinical Investigation* 106(3): 411-420, Aug. 2000.
Kitagawa et al., "Characterization of Mucin-Type Oligosaccharides With the Sialyl-$Le^a$ Structure From Human Colorectal Adenocarcinoma Cells," *Biochem. Biophys. Res. Commun.* 178(3):1429-1436, 1991.
Kitagawa et al., "Immunoaffinity Isolation of a Sialyl-$Le^a$ Oligosaccharide from Human Milk," *J. Biochem.* 104:591-594, 1988.
Kneuer, C. et al., "Selectins—potential pharmacological targets?," *Drug Discovery Today* 11(21/22), Nov. 2006.
Kogan, T.P. et al., "Novel Synthetic Inhibitors of Selectin-Mediated Cell Adhesion: Synthesis of 1,6-Bis[3-(3-carboxymethylphenyl)-r-(2-α-D-mon-nopyranosyloxy)phenyl]hexane (TBC1269)," *J. Med. Chem* 41:1099-1111, 1998.
Kogan, T.P. et al., "Rational Design and Synthesis of Oligosaccharide Mimetics: Selectin Antagonists as Cell Adhesion Inhibitors," *Abstracts of Papers, 210th ACS National Meeting*, American Chemical Society, Chicago, IL, Aug. 20-24, 1995, MEDI-18.
Kogan, T.P. et al., "Rational Design and Synthesis of Small Molecule, Non-oligosaccharide Selectin Inhibitors: (α-D-Mannopyranosyloxy)biphenyl-Substituted Corboxylic Acids," *J. Med. Chem.* 38: 4976-4984, Dec. 22, 1995.
Köhler and Milstein, "Continuous cultures of fused cells secreting antibody of predefined specificity," *Nature* 256:495-497, 1975.
Köhler and Milstein, "Derivation of specific antibody-producing tissue culture and tumor lines by cell fusion," *Eur. J. Immunol.* 6:511-519, 1976.
Kojima and Hakomori, "Specific Interaction between Gangliotriaosylceramide ($G_{g3}$) and Sialosyllactosylceramide ($G_{M3}$) as a Basis for Specific Cellular Recognition between Lymphoma and Melanoma Cells," *J. Biol. Chem.* 264(34):20159-20162, 1989.
Koprowski et al., "Colorectal Carcinoma Antigens Detected by Hybridoma Antibodies," *Somatic Cell Genetics* 5(6):957-972, 1979.
Kuzuoka, "Antitumor activity of murine monoclonal antibody NCC-ST-421," *Chem. Ab.* 115:27344v, 1991.
Lamblin et al., "Primary Structure Determination of Five Sialylated Oligosaccharides Derived from Bronchial Mucus Glycoproteins of Patients Suffering from Cystic Fibrosis. The Occurrence of the NeuAcα(2→3)Galβ(1→4)[Fucα(1→3)]GlcNAcβ(1→•) Structural Element Revealed By 500-Mhz H NMR Spectroscopy," *Journal of Biological Chemistry* 259(14):9051-9058, 1984.
Larsen et al., PADGEM-Dependent Adhesion of Platelets to Monocytes and Neutrophils Is Mediated by a Lineage-Specific Carbohydrate, LNF III (C15), *Cell* 63:467-474, 1990.
Lindenberg et al., "Carbohydrate binding properties of mouse embryos," *J. Reprod. Fert.* 89:431-439, 1990.
Lipartiti et al., "Monosialoganglioside GM1 Reduces NMDA Neurotoxicity in Neonatal Rat Brain," *Experimental Neurology* 113:301-305, 1991.
Lowe et al., "A transfected human fucosyltransferase cDNA determines biosynthesis of oligosaccharide ligand(s) for endothelial-leukocyte adhesion molecule I," *Biochem. Soc. Trans.* 19(3):649-653, 1991.
Lowe et al., "ELAM-1-Dependent Cell Adhesion to Vascular Endothelium Determined by a Transfected Human Fucosyltransferase cDNA," *Cell* 63:475-484, 1990.
Macher et al., "A Novel Carbohydrate, Differentiation Antigen on Fucogangliosides of Human Myeloid Cells Recognized by Monoclonal Antibody VIM-2," *Journal of Biological Chemistry* 263(21):10186-10191, 1988.
Magnani et al., "Identification of the Gastrointestinal and Pancreatic Cancer-associated Antigen Detected by Monoclonal Antibody 19-9 in the Sera of Patients as a Mucin," *Cancer Res.* 43:5489-5492, 1983.
Magnani et al., "A Monoclonal Antibody-defined Antigen Associated with Gastrointestinal Cancer Is a Ganglioside Containing Sialylated Lacto-*N*-fucopentaose II," *Journal of Biological Chemistry* 257(23):14365-14369, 1982.
Magnani, J., "Carbohydrate Sequences Detected by Murine Monoclonal Antibodies," *Chemistry and Physics of Lipids* 42:65-74, 1986.
Magnani, J., "Potent Glycomimetic Inhibitors of the Adhesion Molecule, PA-IIL, for the Bacterial Pathogen, *Pseudomonas auroginosa," Glycobiology* 13(11): 854, Abstract No. 104, Oct. 2003.
Matsui, N.M. et al., "The Novel Adhesion of Erythrocytes to P-Selectin in Sickle Cell Disease," *Blood* 96(11)Pt. 1:600a, Abstract #2575, Nov. 16, 2000.
Matsui, N.M. et al., "Heparin inhibits the flow adhesion of sickle red blood cells to P-selectin," *Blood* 100(10):3790-3796, Nov. 15, 2002.
Matsui, N.M. et al., "P-selectin mediates the adhesion of sickle erythrocytes to the endothelium," *Blood* 98(6): 1955-1962, Sep. 15, 2001.
Mulligan and Berg, "Selection for animal cells that express the *Escherichia coli* gene coding for xanthine-gunine phosphoribosyltransferase," *Proc. Natl. Acad. Sci. USA* 78:2072-2076, 1981.
Nagel, R.L., "A Knockout of a Transgenic Mouse-Animal Models of Sickle Cell Anemia," *The New England Journal of Medicine* 339: 194-195, Jul. 16, 1998.
Natarajan, M.M. et al., "Adhesion of sickle red blood cells and damage to interleukin-1 beta stimulated endothelial cells under flow in vitro," *Blood* 87: 4845-4852, 1996.
Nicolaou et al., "Total Synthesis of the Tumor-Assocaited $Le^x$ Family of Glycosphingolipids," *J. Amer. Chem. Soc.* 112:3693-3695, 1990.
Nudelman et al., "Novel Fucolipids of Human Adenocarcinoma: Disialosyl $Le^a$ Antigen ($III^4FucIII^6NeuAcIV^3NeuAcLc_4$) of Human Colonic Adenocarcinoma and the Monoclonal Antibody (FH7) Defining This Structure," *J. Biol. Chem.* 261:5487-5495, 1986.
Orhlein, R., "Carbohydrates and Derivatives as Potential Drug Candidates with Emphasis on the Selectin and Linear-B Area," *Mini Reviews in Medicinal Chemistry* 1: 349-361, 2001.
Palcic et al., "Enzymic Synthesis of Oligosaccharides Terminating in the Tumor-Associated Sialyl-Lewis-a Determinant," *Carbohydr. Res.* 190:1-11, 1989.
Palcic et al., "Regulation of *N*-Acetylglucosaminyltransferase V Activity. Kinetic Comparisons of Parental, Rous Sarcoma Virus-Transformed BHK, and L-Phytohemagglutinin-Resistant BHK Cells Using Synthetic Substrates and an Inhibitory Substrate Analog," *J. Biol. Chem.* 265:6759-6769, 1990.
Palcic et al., "A Bisubstrate Analog Inhibitor for α(1→2)-Fucosyltransferase," *J. Biol. Chem.* 264:17174-17181, 1989.
Palma-Vargas, J.M. et al., "Small-Molecule Selectin Inhibitor Protects Against Liver Inflammatory Response After Ischemia and Reperfusion," *J. Am. Coll. Surg.* 185: 365-372, 1997.
Perret, S. et al., "Structural basis for the interaction between human milk oligosaccharides and the bacterial lectin PA-IIL of *Pseudomonas aeruginosa," Biochem. J*. 389: 325-332, 2005.
Phillips et al., "ELAM-1 Mediates Cell Adhesion by Recognition of a Carbohydrate Ligand, Sialyl-$Le^x$," *Science* 250:1130-1132, 1990.
Picker et al., "The Neutrophil Selectin LECAM-1 Presents Carbohydrate Ligands to the Vascular Selectins ELAM-1 and GMP-140," *Cell* 66:921-933, 1991.
Prokazova et al., "Sialylated lactosylceramides. Possible inducers of non-specific immunosuppression and atherosclerotic lesions," *European Journal of Biochemistry* 172:1-6, 1988.
Rauvala et al., "Studies on Cell Adhesion and Recognition. I. Extent and Specificity of Cell Adhesion Triggered by Carbohydrate-reactive Proteins (Glycosidases and Lectins) and by Fibronectin," *J. Cell Biol.* 88:127-137, 1981.
Rice and Bevilacqua, "An Inducible Endothelial Cell Surface Glycoprotein Mediates Melanoma Adhesion," *Science* 246:1303-1306, 1989.
Ruoslahti and Pierschbacher, "New Perspectives in Cell Adhesion: RGD and Integrins," *Science* 238:491-497, 1987.
Sakurai et al., "Selection of a Monoclonal Antibody Reactive with a High-Molecular-Weight Glycoprotein Circulating in the Body Fluid of Gastrointestinal Cancer Patients," *Cancer Research* 48:4053-4058, 1988.
Sastry et al., "Cloning of the immunological repertoire in *Escherichia coli* for generation of monoclonal catalytic antibodies: Construction of a heavy chain variable region-specific cDNA library," *Proc. Natl. Acad. Sci. USA* 86:5728-5732, 1989.
Scharfman, A. et al., "*Pseudomonas aeruginosa* binds to neoglycoconjugates bearing mucin carbohydrate determinants and predominantly to sialyl-Lewis x conjugates," *Glycobiology* 9(8): 757-764, 1999.
Scharfman, A. et al., "Recognition of Lewis x Derivatives Present on Mucins by Flagellar Components of *Pseudomonas aeruginosa," Infection and Immunity* 69(9): 5243-5248, Sep. 2001.
Shitara et al., "Application of Anti-Sialyl $Le^a$ Monoclonal antibody, KM231, for Immunotherapy of Cancer," *Anticancer Res.* 11:2003-2014, 1991.
Siuzdak et al., "Examination of the Sialyl Lewis X—Calcium Complex by Electrospray Mass Spectrometry," *Bioorganic & Medicinal Chemistry Letters* 4(24): 2863-2866, 1994.
Solovey, A. et al., "Circulating Activated Endothelial Cells in Sickle Cell Anemia," *The New England Journal of Medicine* 337:1584-1590, Nov. 27, 1997.
Solovey, A.A. et al., "Modulation of endothelial cell activation in sickle cell disease: a pilot study," *Blood* 97(7):1937-1941, Apr. 1, 2001.
Sprengard, U. et al., "Synthesis and Biological Activity of Novel Sialyl-$Lewis^X$Conjugates," *Bioorganic & Medicinal Chemistry Letters* 6(5): 509-514, 1996.
Stanley and Atkinson, "The LEC11 Chinese Hamster Ovary Mutant Synthesizes *N*-Linked Carbohydrates Containing Sialylated, Fucosylated Lactosamine Units. Analysis by One- and Two-Dimensional H NMR Spectroscopy," *J. Biol. Chem.* 263(23):11374-11381, 1988.
Stephens and Cockett, "The construction of highly efficient and versatile set of mammalian expression vectors," *Nucleic Acids Research.* 17:7110, 1989.
Streeter et al., "Immunohistologic and Functional Characterization of a Vascular Addressin Involved in Lymphocyte Homing into Peripheral Lymph Nodes," *Journal of Cell Biology* 107: 1853-1862, 1988.
Stroud et al., "Extended Type 1 Chain Glycosphingolipids: Dimeric $Le^a(III^4V^4Fuc_2Lc_6)$ as Human Tumor-associated Antigen," *J. Biol. Chem.* 266(13):8439-8446, 1991.
Svenson and Lindberg, "Coupling of Acid Labile *Salmonella* Specific Oligosaccharides to Macromolecular Carriers," *J. Immunol. Meth.* 25:323-335, 1979.

Takada et al., "Adhesion of Human Cancer Cells to Vascular Endothelium Mediated by a Carbohydrate Antigen, Sialyl Lewis A[1]," *Biochem. Biophys. Res. Commun.* 179(2):713-719, 1991.

Takeichi, M., "Cadherins: a molecular family essential for selective cell-cell adhesion and animal morphogenesis," *Trends Genet.* 3(8):213-217, 1987.

Thoma, G. et al., "A readily Available, Highly Potent E-Selectin Antagonist," *Angew. Chem. Int. Ed.* 40(19): 3644-3647, 2001.

Thoma, G. et al., "Preorganization of the Bioactive Conformation of Sialyl Lewis$^x$ Analogues Correlates with Their Affinity to E-Selectin,"*Angew. Chem. Int. Ed.* 40(10): 1941-1945, 2001.

Thoma, G. et al., "Synthesis and Biological Evaluation of a Sialyl Lewis X Mimic with Significantly Improved E-selectin Inhibition," *Bioorganic & Medicinal Chemistry Letters* 11: 923-925, 2001.

Thoma, G. et al., "Synthesis and Biological Evaluation of a Potent E-Selectin Antagonist," *Journal of Medicinal Chemistry* 42(23): 4909-4913, 1999.

Tilton, R.G., "Endotoxin-Induced Leukocyte Accumulation in Aqueous Fluid of Rats is Decreased by a Small Molecule Selectin," *Investigative Opthalmology & Visual Science* 37(3): S918, Abstract No. 4227, Feb. 15, 1996.

Trouet et al., "A covalent linkage between daunorubicin and proteins that is stable in serum and reversible by lysosomal hydrolases, as required for a lysosomotropic drug-carrier conjugate: In vitro and in vivo studies," *Proc. Natl. Acad. Sci. USA* 79:626-629, 1982.

Turhan, A. et al., "Primary role for adherent leukocytes in sickle cell vascular occlusion: A new paradigm," *Proceedings of the National Academy of Sciences of the United States of America* 99(5):3047-3051, Mar. 5, 2002.

Tyrrell et al., "Structural requirements for the carbohydrate ligand of E-selectin," *Proc. Natl. Acad. Sci. USA* 88:10372-10376, 1991.

Waldmann, H. et al., "Synthesis of 2-Acetamindo-2-Deoxyglucosylasparagine Glyco-Tripeptide and —Pentapeptides By Selective C- and N-Terminal Elongation of the Peptide Chain," *Carbohydrate Research* 196: 75-93, 1990.

Walz et al., "Recognition by ELAM-1 of the Sialyl-Le$^x$ Determinant on Myeloid and Tumor Cells," *Science* 250:1132-1135, 1990.

Ward and Mulligan, "Blocking of adhesion molecules in vivo as anti-inflammatory therapy," *Immunology* 1: 165-171, 1994.

Whisler and Yates, "Regulation of Lymphocyte Responses by Human Gangliosides. I. Characteristics of Inhibitory Effects and the Induction of Impaired Activation," *Journal of Immunology* 125(5):2106-2111, 1980.

Yamazaki, F. et al., "Syntheisis of an appropriately protected core glycotetraoside, a key intermediate for the synthesis of 'bisected' complex-type glycans of a glycoprotein," *Carbohydrate Research* 201: 15-30, 1990.

Zhou et al., "The Selectin GMP-140 Binds to Sialylated, Fucosylated Lactosaminoglycans on Both Myeloid and Nonmyeloid Cells," *Journal of Cell Biology* 115(2):557-564, 1991.

Zopf et al., "Affinity Purification of Antibodies Using Oligosaccharide-Phenethylamine Derivatives Coupled to Sepharose," *Meth. Enzymol.* 50:171-175, 1978.

* cited by examiner

BASA 2 1 3 4

XX

COMPOUNDS AND METHODS FOR TREATMENT OF SICKLE CELL DISEASE OR COMPLICATIONS ASSOCIATED THEREWITH

CROSS-REFERENCE TO RELATED APPLICATION

This application claims the benefit under 35 U.S.C. §119 (e) of U.S. Provisional Patent Application No. 60/959,984 filed Jul. 18, 2007; which application is incorporated herein by reference in its entirety.

BACKGROUND

1. Technical Field

The present invention relates generally to compounds, compositions and methods for treating sickle cell disease or complications associated therewith, and more specifically to the use of particular glycomimetics for the treatment. The glycomimetics may also be used to treat graft versus host disease.

2. Description of the Related Art

Sickle cell disease is an inheritable hematological disorder based on a mutation in the β-globin gene of hemoglobin. Upon deoxygenation, this mutated hemoglobin polymerizes and causes a shape change (sickling) of the red blood cell. This change in red blood cells leads to obstruction of blood vessels causing a wide variety of complications such as stroke, pulmonary hypertension, end-organ disease and death.

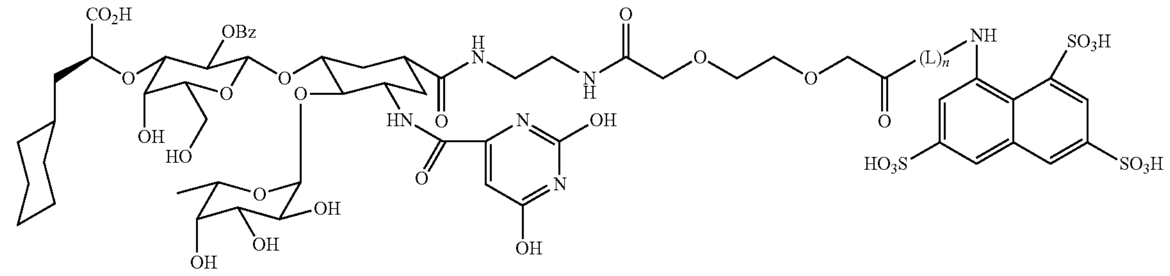

In addition to the fatal or potentially fatal complications, there are serious non-fatal complications of sickle cell disease such as pain. The severity of the pain may vary, but normally requires some form of medical attention. Hospitalization may be necessary.

In the U.S. alone, approximately 70,000-80,000 people suffer from sickle cell disease. Sickle cell disease is estimated to affect one of every 1,300 infants in the general population, and one of every 400 of African descent. Currently, there is no cure for sickle cell disease. The disease is chronic and life-long. Life expectancy is typically shortened.

Accordingly, there is a need in the art for the treatment of sickle cell disease or the complications associated therewith. The present invention fulfills these needs and further provides other related advantages.

BRIEF SUMMARY

Briefly stated, compounds, compositions and methods for treating sickle cell disease or the complications associated therewith, or graft versus host disease, are provided. In the present invention, the compounds used for treatment comprise, or consist of, a particular glycomimetic. Such a compound may be combined with a pharmaceutically acceptable carrier or diluent to form a pharmaceutical composition.

In one embodiment, the present invention provides a method for the treatment of sickle cell disease or a complication associated therewith in an individual who is in need thereof, comprising administering to the individual a compound in an amount effective for treatment, the compound with the formula:

wherein

L=linker group; and n=0-1.

In one embodiment, the present invention provides a method for the treatment of graft versus host disease in an individual who is in need thereof, comprising administering to the individual a compound in an amount effective for treatment, the compound with the formula:

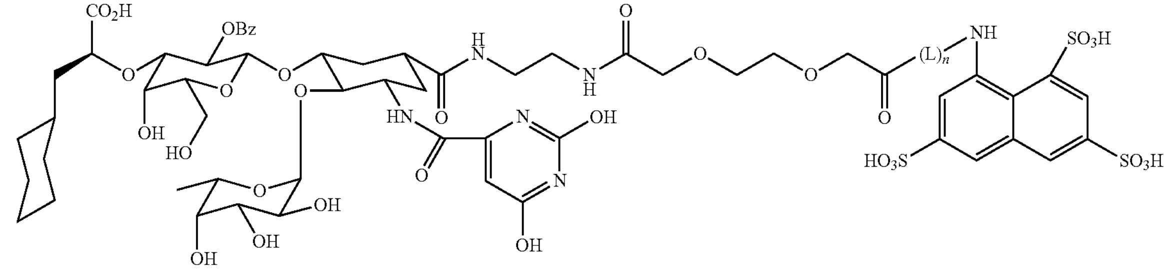

wherein

L=linker group; and n=0-1.

In other embodiments, the above compounds or compositions thereof may be used in the manufacture of a medicament, for any of the uses recited herein.

These and other aspects of the present invention will become apparent upon reference to the following detailed description and attached drawings. All references disclosed herein are hereby incorporated by reference in their entirety as if each was incorporated individually.

DETAILED DESCRIPTION

As noted above, the present invention provides compounds, compositions and methods for the treatment of sickle cell disease or a complication associated therewith, or graft versus host disease, in an individual.

Compounds useful in the compositions and methods of the present invention include embodiments with the formula:

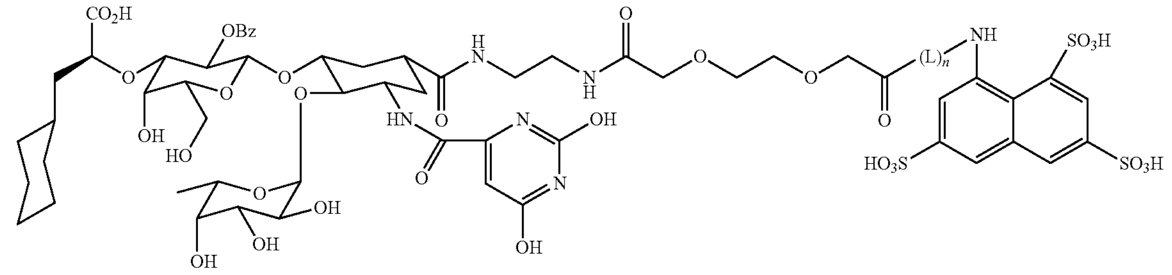

Figure 8:
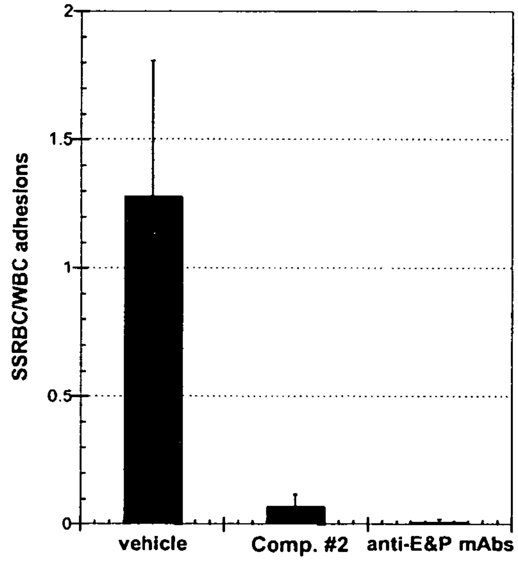
Figure 9:
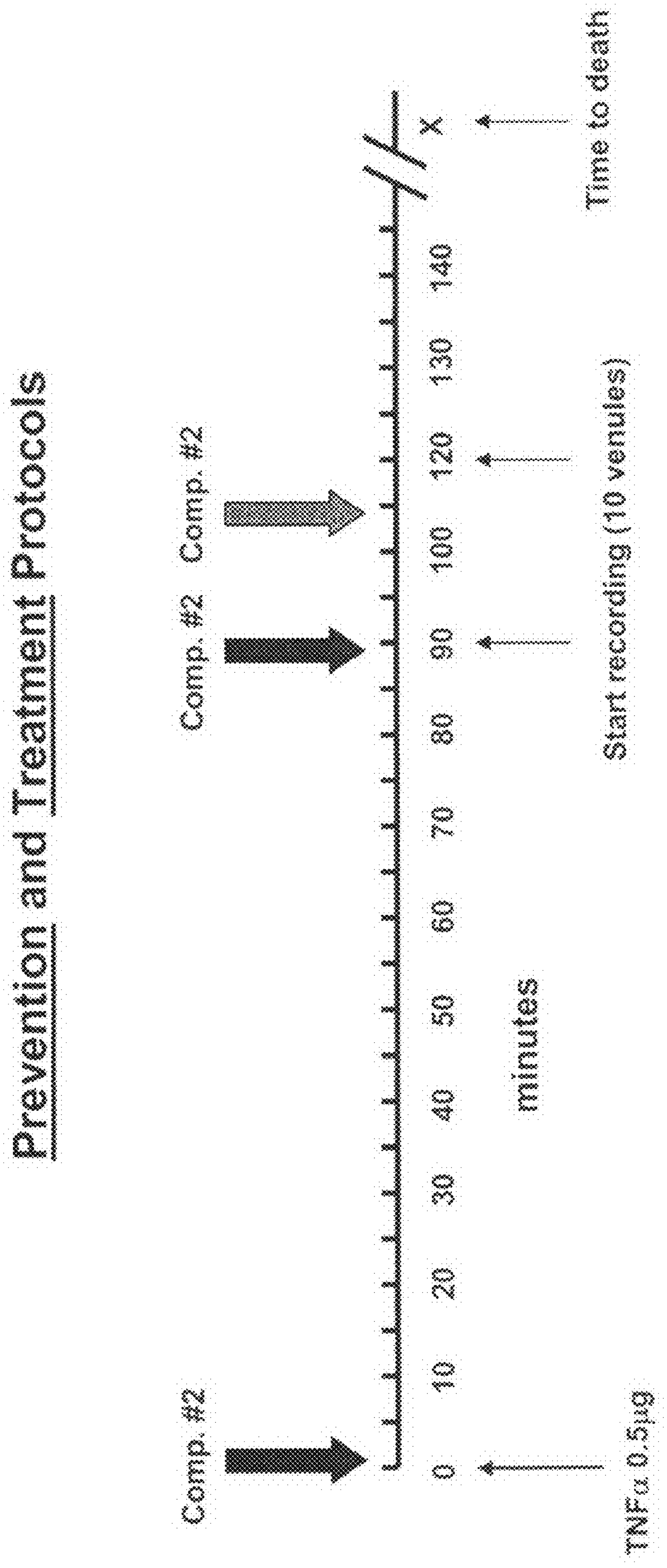
FIG. 9 is a schematic of a sickle cell mouse model for use with both prevention and treatment protocols. The black arrows underneath Comp. #2 are for the prevention protocol. The gray arrow underneath Comp. #2 is for the treatment protocol. Recording is started at the 90 minute mark for the prevention protocol. Recording is started at the 120 minute mark for the treatment protocol.
Figure 10:
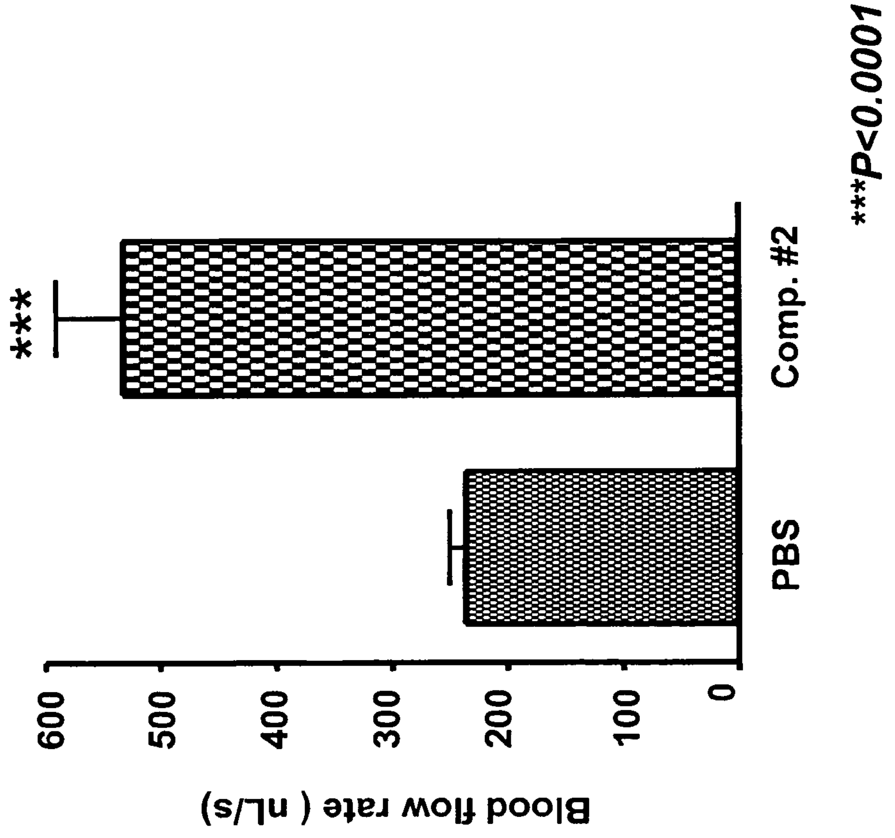
FIG. 10 shows the effects of a compound on delayed treatment of VOC in sickle cell mice as measured by blood flow rate. Compound #2 normalizes the rate of blood flow. The control is phosphate buffered saline (PBS) without compound.
Figure 11:
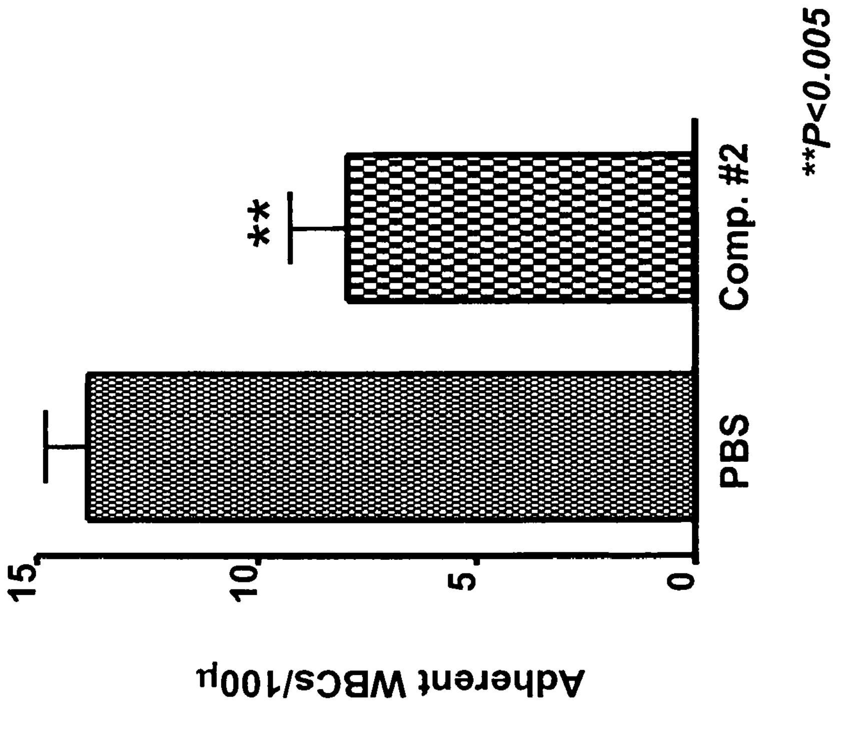
FIG. 11 shows the effects of a compound on delayed treatment of VOC in sickle cell mice as measured by adherent white blood cells (WBCs). Compound #2 causes a significant reduction in the number of WBCs adherent to the vascular endothelium. The control is PBS without compound.
Figure 12:
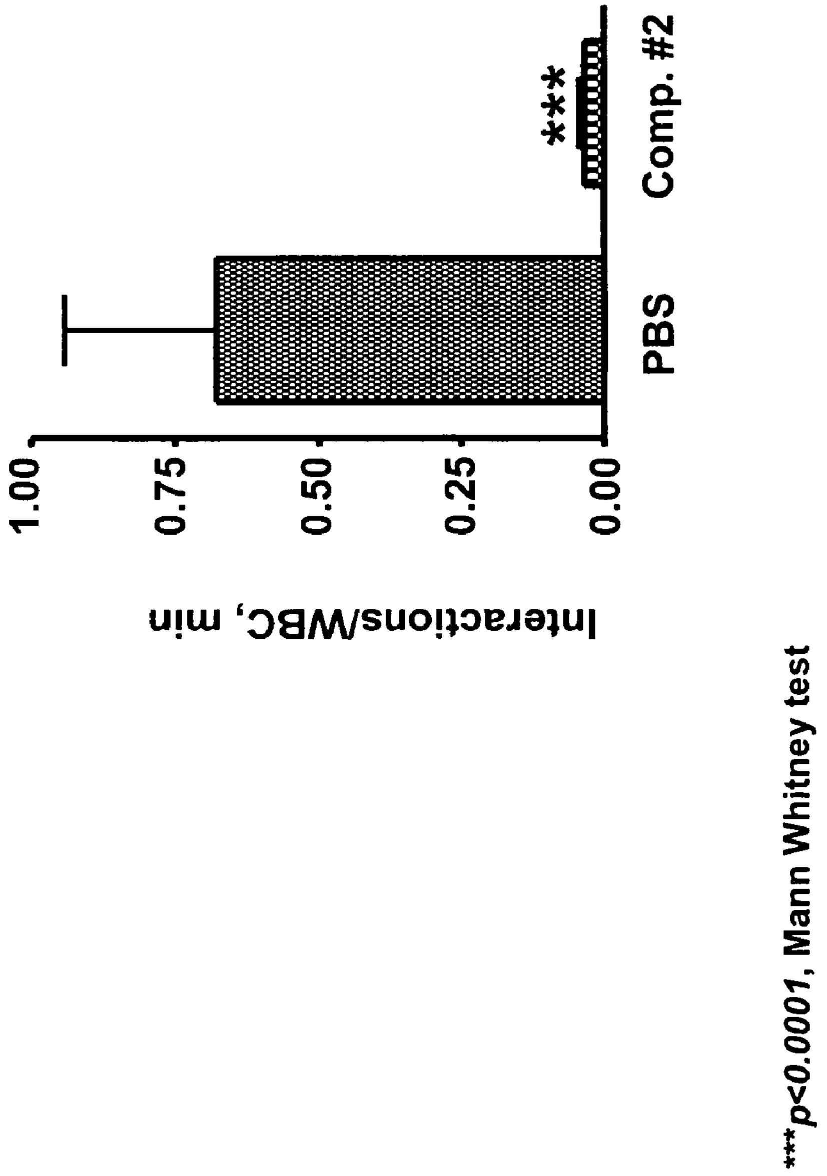
FIG. 12 shows the effects of a compound on delayed treatment of VOC in sickle cell mice as measured by interactions of sickle red blood cells (RBCs) with leukocytes (white blood cells). Compound #2 dramatically reduces interactions of sickle RBCs with leukocytes. The control is PBS without compound.
Figure 13:
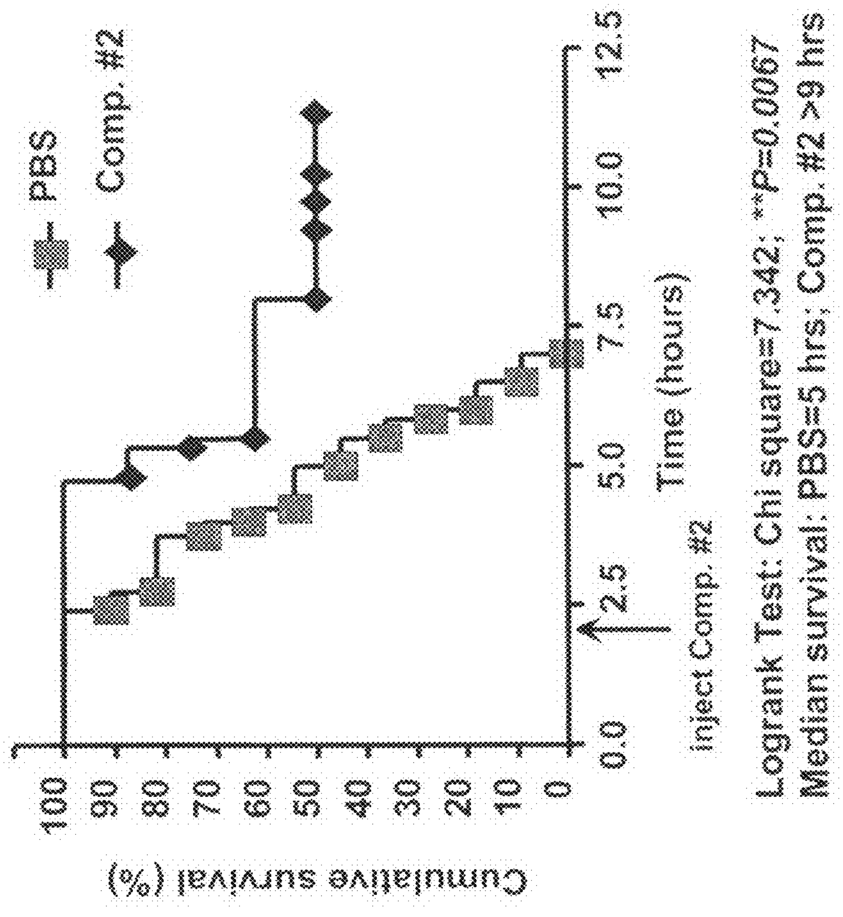
FIG. 13 depicts Kaplan-Meier survival curves. The curve with black diamond symbols is for Compound #2. The curve with gray squares is for the control of PBS without compound.

FIG. 8 shows the effects of a compound or anti-E&P monoclonal antibodies on the adhesion of sickle red blood cells to leukocytes in sickle cell mice in which a vaso-occlusive crisis was induced.

In the above formula, "L" represents a linker. There may be no linkers present (i.e., "n" is 0) or a linker may be present (i.e., "n" is 1). Where no linker is present, the compound is with the formula:

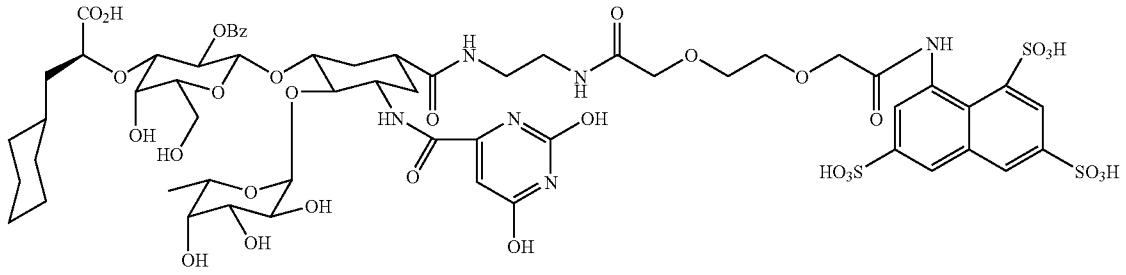

Where n is 1, a linker is present. A linker may include a spacer group, such as $-(CH_2)_p-$ or $-O(CH_2)_p-$ where p is generally about 1-20 (including any whole integer range therein). Other examples of spacer groups include a carbonyl or carbonyl containing group such as an amide.

Embodiments of linkers include the following:

In another embodiment, the linker is

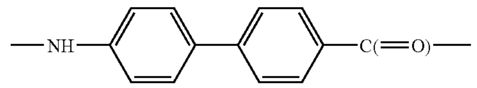

which produces:

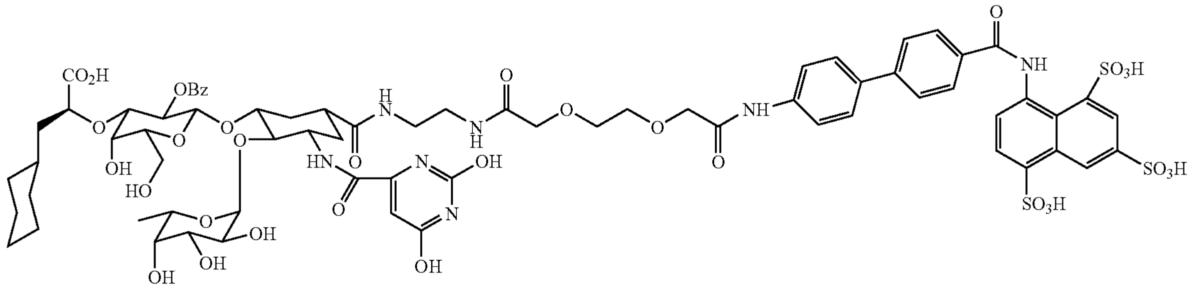

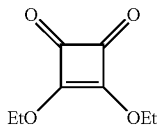

Squaric acid

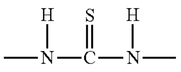

Thiourea

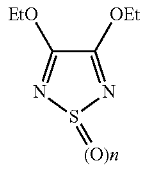

Dithiadiazoleoxide

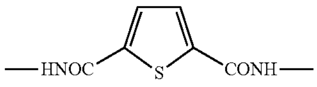

Acylation via Thiofuran

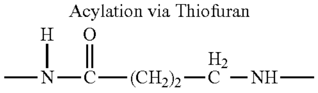

N-Pentenoylation and Reductive amination

-continued

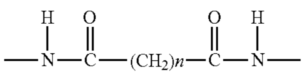

Coupling Via Bifunctional NHS reagent

Other linkers, e.g., polyethylene glycols (PEG) or $-C(=O)-NH-(CH_2)_p-C(=O)-NH_2$ where p is as defined above, will be familiar to those in the art or in possession of the present disclosure.

In another embodiment, the linker is

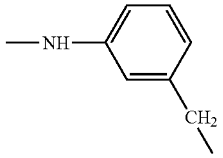

which produces:

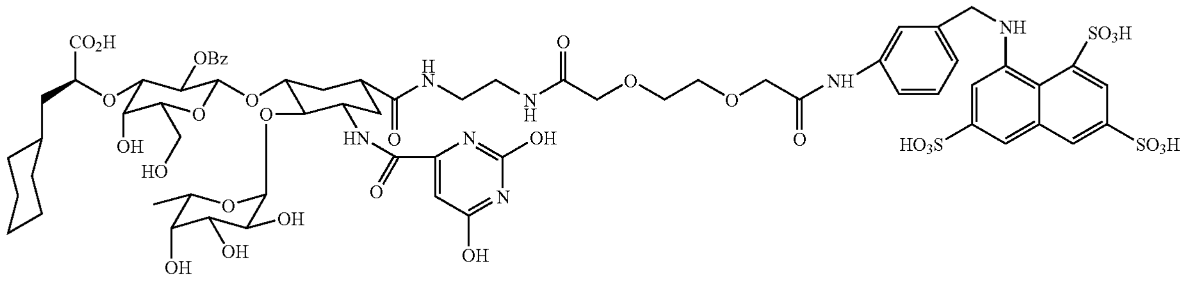

All compounds of the present invention or useful thereto (e.g., for pharmaceutical compositions or methods of treating), include physiologically acceptable salts thereof. Examples of such salts are Na, K, Li, Mg, Ca and Cl.

Compounds as described herein may be present within a pharmaceutical composition. A pharmaceutical composition comprises one or more compounds in combination with (i.e., not covalently bonded to) one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. Compositions of the present invention may be formulated for any appropriate manner of administration, including for example, topical, oral, nasal, intravenous, intracranial, intraperitoneal, subcutaneous, or intramuscular administration.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of compound release. The amount of compound contained within a sustained release formulation depends upon the site of implantation, the rate and expected duration of release and the nature of the condition to be treated or prevented.

The above described compounds including equivalents thereof are useful in methods of the present invention as it relates to sickle cell disease and as it relates to graft versus host disease. In an embodiment, an individual who is in need of treatment for sickle cell disease or a complication associated therewith is administered at least one (i.e., one or more) of the above described compounds in an amount effective for the treatment. As used herein, the term "treatment" (including variations such as "treating") includes prevention. For example, a complication associated with sickle cell disease may not have presented itself in an individual with the disease, and a compound may be administered to prevent presentation of the complication in the individual. Sickle cell disease and complications associated therewith include, for example, anemia, red blood cells becoming stuck in blood vessels, ischemia, infarction, stroke, acute chest crisis, splenic sequestration crisis, shortened life expectancy, organ damage and periodic or chronic pain.

In another embodiment, an individual who is in need of treatment for graft versus host disease (GVHD) is administered at least one (i.e., one or more) of the above-described compounds in an amount effective for the treatment. GVHD commonly arises in patients post stem cell transplantation. A preferred route of administration is via an orally available formulation.

The term "treatment," as set forth above, refers to any of a variety of positive effects from the treatment including, for example, eradicating a complication associated with the disease, relieving to some extent a complication, slowing or stopping progression of the disease, and prolonging the survival time of the recipient. The treatment may be used in conjunction with one or more other therapies for sickle cell disease or complications associated therewith, or therapies for graft versus host disease.

The above described compounds may be administered in a manner appropriate to the disease to be treated. Appropriate dosages and a suitable duration and frequency of administration may be determined by such factors as the condition of the patient, the type and severity of the patient's disease and the method of administration. In general, an appropriate dosage and treatment regimen provides the compound(s) in an amount sufficient to provide therapeutic and/or prophylactic benefit. Within particularly preferred embodiments of the invention, a compound may be administered at a dosage ranging from 0.001 to 1000 mg/kg body weight (more typically 0.01 to 1000 mg/kg), on a regimen of single or multiple daily doses. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated, which will be familiar to those of ordinary skill in the art.

The following Examples are offered by way of illustration and not by way of limitation.

EXAMPLES

Example 1

Figure 1:
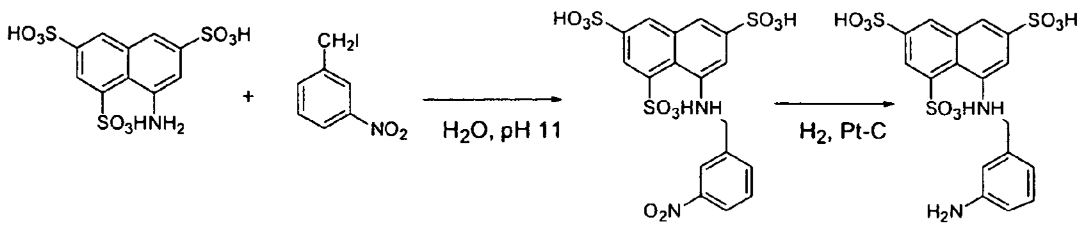
FIG. 1 is a diagram illustrating the synthesis of a component of Compound #1.

Synthesis of BASA (FIG. 1)

Synthesis of compound 4: 3-nitro-benzyl iodide (1) (48.3 g) is added to an aqueous solution (pH 11) of commercially available (Aldrich Chemical Co., Milwaukee, Wis.), 8-aminonaphthalene-1,3,5-trisulfonic acid (2) (29.5 g) with stirring at room temperature. pH of the solution is adjusted to 1 and after evaporation of the solvent, the product 3 (6.4 g) is precipitated out from ethanol.

Platinum catalyzed hydrogenation of compound 3 affords compound 4 (the BASA of FIG. 1) in 96% yield.

Example 2

Figure 2:
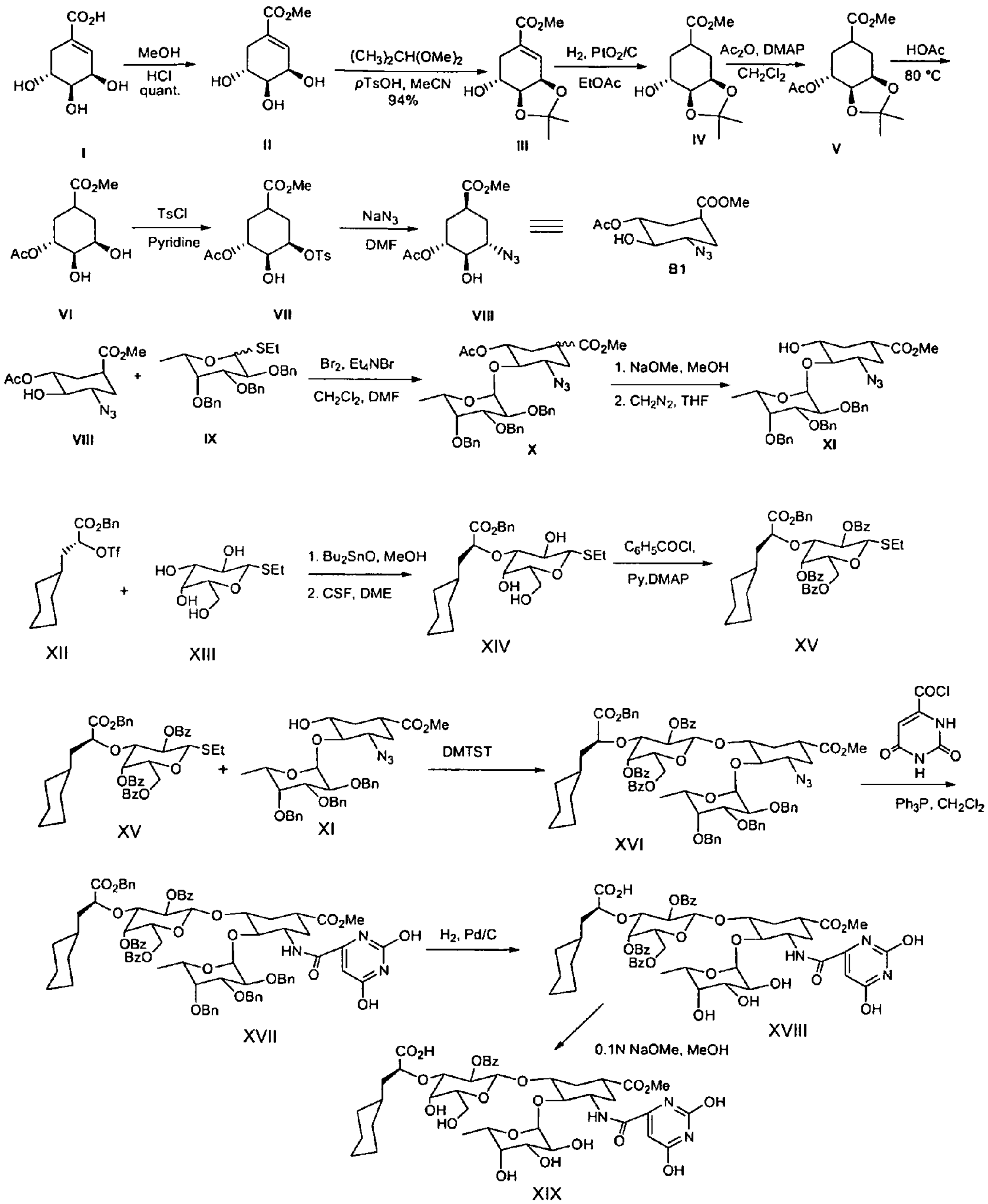
FIG. 2 is a diagram illustrating the synthesis of a component of Compound #1.

Synthesis of Glycomimetic (FIG. 2)

Synthesis of intermediate II: (−)-Shikimic acid (20 g) in MeOH (200 ml) and sulfuric acid (2 ml, 98%) are stirred at room temperature (rt) for 50 h. The reaction mixture is neutralized with 2N aqueous NaOH in the cold. After evaporation to dryness, the residue is purified by silica gel chromatography to afford II (19.2 g).

Synthesis of intermediate III: Methyl shikimate (II, 10 g), 2,2 dimethoxypropane (10 ml) and p-TsOH (0.8 g) are dissolved in acetonitrile (125 ml) and stirred at rt for 1 h. The reaction mixture is then neutralized with triethylamine (2 ml) and evaporated to dryness. The residue is chromatographed on silica gel to yield III (11 g).

Synthesis of intermediate IV: The shikimic acid derivative III (10 g) and $PtO_2$/C (10%, 250 mg) in MeOH (40 ml) are hydrogenated at rt under vigorous stirring. After 16 h the reaction mixture is filtered over celite and evaporated to dryness. The residue is chromatographed on silica gel to yield IV.

Synthesis of intermediate V: To a solution of IV (8 g) in DCM (100 ml) at 0° C. are added pyridine (12 ml), acetic anhydride (7 ml) and a DMAP (25 mg). The reaction mixture is stirred at rt for 1 h, and diluted with EtOAc (250 ml). After washing with 0.5 M aqueous HCl (3×50 ml), saturated solution of $KHCO_3$ (3×50 ml) and brine (3×50 ml), the combined organic layers are dried ($Na_2SO_4$) and evaporated to dryness. The residue is purified by chromatography on silica gel to yield V (6.8 g).

Synthesis of intermediate VI: A solution of V (6.0 g) in acetic acid (30 ml, 80%) is stirred at 80° C. for 1 h. Solvent is evaporated off and the residue is purified by chromatography on silica gel (DCM/MeOH 14:1) to yield VI (3.6 g).

Synthesis of intermediate VII: A solution of VI (3 g) and p-TsCl (3.5 g) in pyridine (30 ml) is stirred at rt for 6 h. MeOH (5 ml) is added and the solvent is evaporated at reduced pressure, the residue dissolved in EtOAc (3×150 ml) and the organic layers are washed with 0.5 M aqueous HCl (0° C.), water (cold) and brine (cold). The combined organic layers are dried ($Na_2SO_4$), filtered on Celite and evaporated to dryness. The residue is purified by chromatography on silica gel (toluene/EtOAc 4:1) to yield VII (3.7 g).

Synthesis of compound VIII: A solution of VII (3 g) and $NaN_3$ (2.5 g) in DMF (20 ml) is stirred at 80° C. The reaction mixture is cooled to rt and diluted with EtOAc (200 ml) and water (50 ml). The organic layer is additionally washed twice with water (2×50 ml) and once with brine (50 ml). All aqueous layers are extracted twice with EtOAc (2×50 ml). The combined organic layers are dried with $Na_2SO_4$, filtered and the solvent is evaporated off. The residue is purified by chromatography on silica gel (petroleum ether/EtOAc 5:2) to give VIII (2.2 g).

Synthesis of compound X: To a solution of ethyl 2,3,4-tri-O-benzyl-α-L-fucothiopyanoside IX (1.5 g) in DCM (3 ml), bromine (150 μl) is added at 0° C. under argon. After 5 min the cooling bath is removed and the reaction mixture is stirred for additional 25 min at rt. Cyclohexene (200 μl) is added and the reaction mixture is added to a solution of VIII (400 mg), $(Et)_4NBr$ (750 mg) and powdered 4 Å molecular sieves in DCM (10 ml) and DMF (5 ml). After 16 h, triethylamine (1.5 ml) is added and stirred for an additional for 10 min, diluted with EtOAc (50 ml) and washed with sat. aqueous $NaHCO_3$, water and brine. The aqueous layers are extracted twice with EtOAc (2×50 ml). The combined organic layers are dried ($Na_2SO_4$), filtered and evaporated to dryness. The residue is purified by chromatography on silica gel (toluene/EtOAc 9:1) to yield X (700 mg).

Synthesis of compound XI: To a solution of X (1.5 g) in MeOH (20 ml) is added freshly prepared NaOMe (80 mg) and the reaction mixture is stirred in a pressure tube at 80° C. for 20 h. The reaction mixture is cooled to rt and neutralized with acetic acid. Solvent is evaporated to dryness and the residue is dissolved in ether. Freshly prepared diazomethane is added and the excess diazomethane is neutralized with acetic acid. Solvent is evaporated off to give XI (1.25 g).

Synthesis of building block XV: This synthesis is done exactly in same way as described previously (*Helvetica Chemica Acta* 83:2893-2907 (2000)).

Synthesis of compound XVI: A mixture of XI (1.6 g), XV (3 g) and activated powdered molecular sieves 4 Å (1 g) in DCM (17 ml) is stirred at rt under argon for 2 h. Then DMTST (2 g) is added in 4 equal portions over a period of 1.5 h. After 24 h the reaction mixture is filtered over Celite and the filtrate is diluted with DCM (100 ml). The organic layer is washed with sat. aqueous $NaHCO_3$ and brine and the aqueous layers are extracted twice with DCM. The combined organic layers are dried ($Na_2SO_4$), filtered and evaporated to dryness. The residue is purified by chromatography on silica gel (toluene/EtOAc 8:1) to yield XVI (1.5 g).

Synthesis of compound XVII: To a solution of XVI (500 mg) and orotic acid chloride (500 mg) in dichloromethane (10 ml) is added a solution of triphenylphosphine (500 mg in 5 ml dichloromethane) dropwise during 10 min. The reaction mixture is stirred at rt for 25 h and the solvent is evaporated off. The residue is purified (chromatography on silica gel DCM/MeOH 19:1) to give XVII (250 mg).

Synthesis of compound XVIII: To a solution of XVII (200 mg) in dioxane-water (5:1, 12 ml) is added 10% Pd—C (100 mg) and the reaction mixture is stirred vigorously under hydrogen (55 psi) for 24 h. Catalyst is filtered through a bed of celite and the solvent is evaporated off. Residue is purified by silica gel chromatography to give compound XVIII (150 mg).

Synthesis of XIX: To a solution of compound XVIII (145 mg) in MeOH (5 ml) is added a solution of NaOMe in MeOH (25%, 0.025 ml) and the reaction mixture is stirred at rt for 4 h, neutralized with acetic acid and the solvent is evaporated off. Residue is dissolved in water and passed through a bed of Dowex 50wX-8 (Na-form) resin. Water wash is evaporated off to afford compound XIX (100 mg).

Synthesis of EDA-XIX: XIX (80 mg) is heated at 70° C. with ethylenediamine (EDA) (1 ml) with stirring for 5 h. Solvent is evaporated off and the purified by sephadex G-25 column to give EDA-XIX (82 mg).

Example 3

Figure 3:
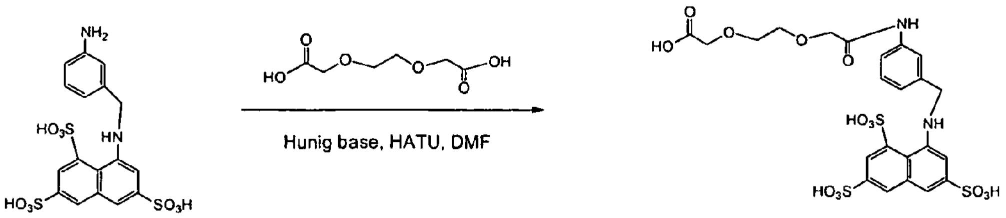
FIG. 3 is a diagram illustrating the modification of the component of FIG. 1.

Synthesis of PEGylated BASA (FIG. 3)

To a solution of 3,6-dioxaoctanedioic acid (PEG, 200 mg, Aldrich Chemical Co., Milwaukee, Wis.) in DMF (1 ml) is added Hunig base (0.4 ml), and then HATU (0.35 g) is added after 5 min. The solution is stirred at RT for 10 min. and then a solution of the BASA of Example 2 (50 mg) in DMF (0.1 ml) is added. The reaction mixture is stirred for 4 h at rt and the solvent is evaporated off. The residue is purified by hplc (reverse-phase C18 column) to give XX (40 mg).

Example 4

Figure 4:
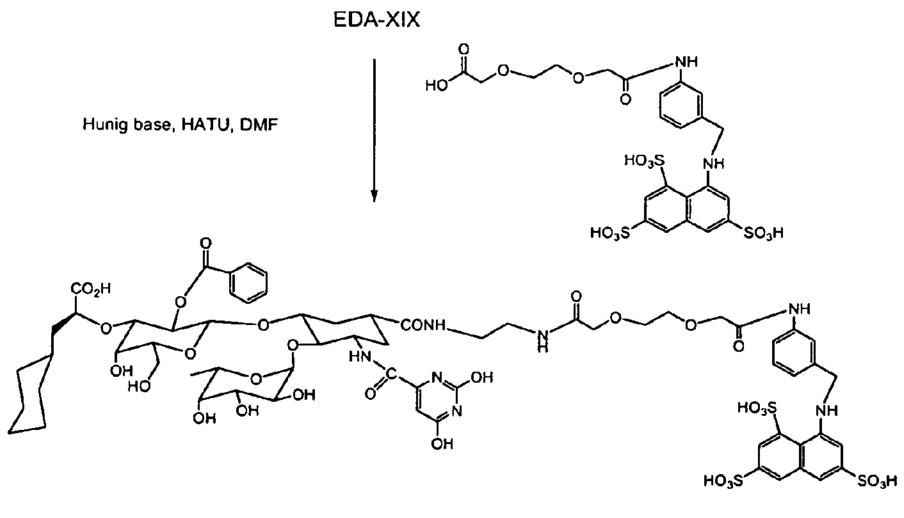
FIG. 4 is a diagram illustrating the reaction of the components of FIGS. 2 and 3 to form Compound #1. Compound XIX of FIG. 2 is reacted with ethylenediamine (EDA) to form EDA-XIX.

Synthesis of Glycomimetic-BASA Compound #1 (FIG. 4)

To a solution of XX from Example 3 (0.015 g) in DMF (0.1 ml), is added Hunig base (0.015 ml) and then HATU (0.007 g). The reaction mixture is stirred for 10 min at RT. A solution of EDA-XIX from Example 2 (0.010 g in DMF ml) is added and the reaction mixture is stirred at RT for 8 h. Solvent is evaporated off and the residue is purified by sephadex G-25 chromatography to give Glycomimetic-BASA #1 of FIG. 4 (0.008 g).

Example 5

Figure 5:
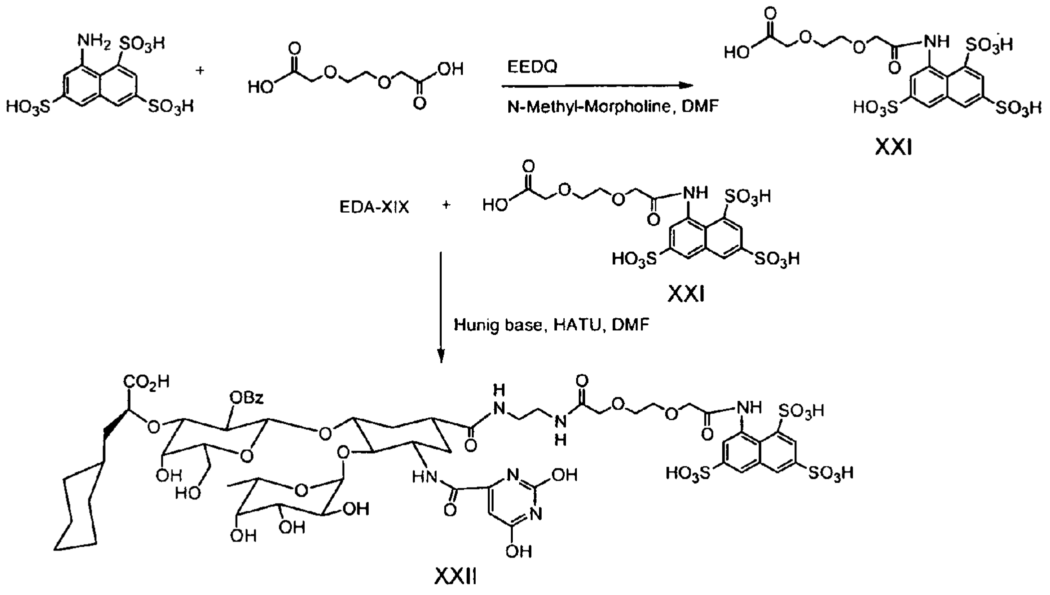
FIG. 5 is a diagram illustrating the synthesis of Compound #2. Compound XIX of FIG. 2 is reacted with ethylenediamine (EDA) to form EDA-XIX.

Synthesis of Glycomimetic-BASA Compound #2 (FIG. 5)

Synthesis of compound XXI: To a solution of 3,6-dioxaoctanedioic acid (PEG, 200 mg, available commercially) in DMF (1 ml) is added Hunig base (0.4 ml) and then HATU (0.35 g) is added after 5 min. The solution is stirred at RT for 10 min and then solution of 8-aminonaphthalene-1,3,6-trisulfonic acid (50 mg, available commercially) in DMF is added. The reaction mixture is stirred for 4 h at RT and the solvent is evaporated off. The residue is purified by hplc (reverse-phase C18 column) to give XXI (25 mg).

Synthesis of compound XXII: This synthesis is performed in the same way as described in example 4 except using EDA-XIX from example 2 and XXI to give compound XXII (4 mg).

Example 6

Effects of Compound # 2 on Microvascular Flow in Sickle Cell Mice as Determined by Intravital Microscopy Sickle cell disease is a genetic condition caused by a point mutation ($\beta^s$) in the β-chain of hemoglobin. This single mutation leads to abnormal microvascular flow, endothelial activation and episodic vaso-occlusion. Impairment of blood flow is responsible for the severe pain, end organ damage and eventual death of these patients.

Figure 6:
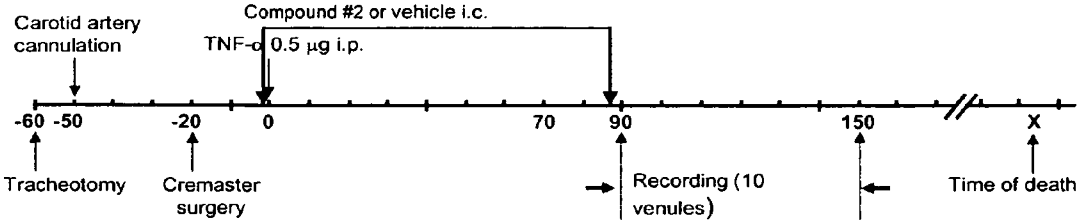
FIG. 6 is a schematic of the protocol for inducing a vaso-occlusive crisis (VOC) in sickle cell-affected mice and recording blood flow.

An animal model of sickle cell disease exists in fully chimeric mice constructed by bone marrow transplantation and expressing >97% human globin containing the $\beta^s$ mutation. A vaso-occlusive crisis is induced by stimulation with TNFα and is monitored by observing and recording blood flow by intravital microscopy of the venules in the cremaster muscle. A schematic diagram of the protocol is shown in FIG. 6.

Each mouse is prepared by cannulating the right carotid artery and by undergoing a tracheotomy to facilitate ventilation under anesthesia. Twenty (20) minutes prior to stimulation with TNFα, the cremaster muscle is gently exteriorized and the venules are set on a microscope stage for observation and recording of blood flow. Just prior to administration of TNFα and again prior to the recording of the venules (90 min later), Compound # 2 is administered through the cannulated carotid artery and data is obtained by monitoring blood flow and recording time of death.

Figure 7:
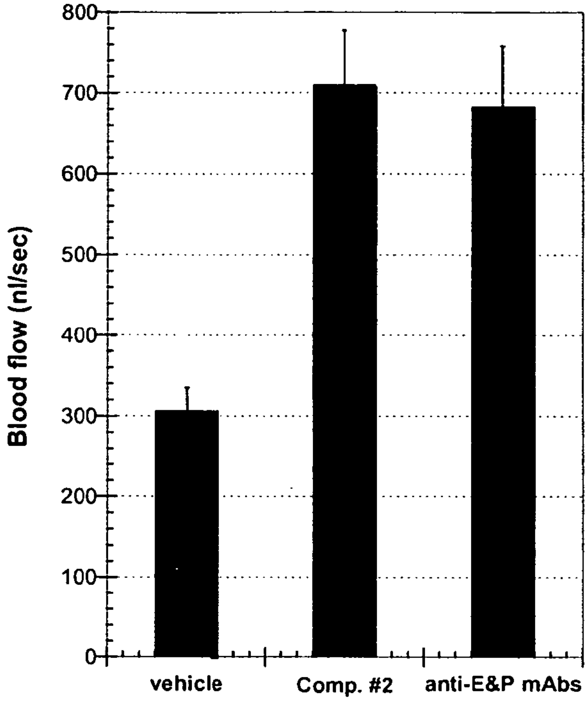
FIG. 7 shows the effects of a compound or anti-E&P monoclonal antibodies on blood flow in the sickle cell mouse.

The effects of Compound # 2 on blood flow in the sickle cell mouse are shown in FIG. 7. In the control mice, in which only vehicle is injected, blood flow is very slow and indicative of the sickle disease state after stimulation with TNFα. Either Compound # 2 or a mixture of antibodies against E- and P-selectin have dramatic effects by restoring blood flow to a velocity observed in normal mice.

During a vaso-occlusive crisis which is simulated in the sickle cell mouse model, blood cells adhere to each other, form aggregates, and decrease blood flow to vital organs, resulting in organ failure, and in severe cases, death. The effects of Compound # 2 on the adhesion of sickle red blood cells (RBC) to leukocytes was determined in sickle cell mice in which TNFα was used to induce a vaso-occlusive crisis. As shown in FIG. 8, both Compound # 2 and a mixture of antibodies against E- and P-selectins provide significant inhibition of adhesion among these cell types.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

The invention claimed is:

1. A method for the treatment of sickle cell disease or a complication associated therewith in an individual who is in need thereof, comprising administering to the individual a compound in an amount effective for treatment, the compound with the formula:

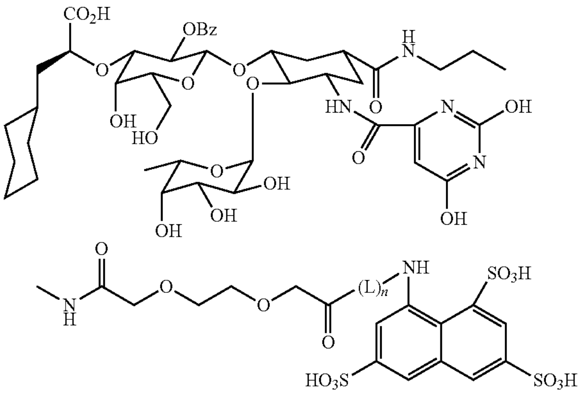

wherein

L=linker group; and n=0-1.

2. The method according to claim 1 wherein in the compound n=0.

3. The method according to claim 1 wherein in the compound n=1 and L is

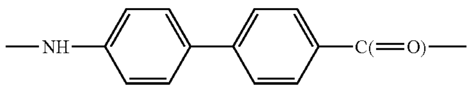

where the N of L is attached to terminal C of C(=O) of the compound.

4. The method according to claim 1 wherein in the compound n=1 and L is

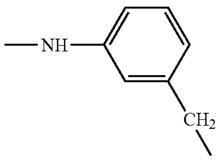

where the N of L is attached to terminal C of C(=O) of the compound.

5. The method of any one of claims 1-4 wherein the compound is in combination with a pharmaceutically acceptable carrier or diluent.

* * * * *